United States Patent
Sonenblum et al.

(10) Patent No.: US 10,357,186 B2
(45) Date of Patent: Jul. 23, 2019

(54) WHEELCHAIR IN-SEAT ACTIVITY TRACKER

(71) Applicants: Sharon E. Sonenblum, Atlanta, GA (US); Stephen Sprigle, Atlanta, GA (US); James S. Martin, Atlanta, GA (US)

(72) Inventors: Sharon E. Sonenblum, Atlanta, GA (US); Stephen Sprigle, Atlanta, GA (US); James S. Martin, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 15/672,688

(22) Filed: Aug. 9, 2017

(65) Prior Publication Data

US 2018/0042525 A1    Feb. 15, 2018

Related U.S. Application Data (60) Provisional application No. 62/372,331, filed on Aug. 9, 2016.

(51) Int. Cl.
*A61B 5/11* (2006.01)
*G08B 21/04* (2006.01)
(Continued)

(52) U.S. Cl.
CPC .......... *A61B 5/1116* (2013.01); *A61B 5/0015* (2013.01); *A61B 5/1036* (2013.01); *A61B 5/6892* (2013.01); *A61B 5/6894* (2013.01); *A61B 5/72* (2013.01); *A61B 5/7264* (2013.01); *A61B 5/746* (2013.01); *G08B 21/0461* (2013.01); *A61B 5/0002* (2013.01); *A61B 2505/09* (2013.01); *A61B 2562/0247* (2013.01); *A61B 2562/04* (2013.01)

(58) Field of Classification Search
CPC ... A61B 5/1116; A61B 5/6894; A61B 5/0015; A61B 5/72; A61B 5/746; G08B 21/0461
See application file for complete search history.

(56) References Cited

U.S. PATENT DOCUMENTS

7,311,675 B2 * 12/2007 Peifer ................... A61B 5/1118
                                                                600/587
7,733,224 B2    6/2010 Tran
(Continued)

*Primary Examiner* — Ryan W Sherwin
(74) *Attorney, Agent, or Firm* — Bryan W. Bockhop; Bockhop Intellectual Property Law, LLC (57) ABSTRACT

In a system for determining in-seat behavior of a user, a sensor mat is placed on a location of the seat. The sensor mat includes a plurality of sensors that are distributed anthropometrically so as to be placed below predetermined anatomical sites of a typical user. At least one training episode in which the user assumes at least one predetermined posture for a predetermined amount of time is executed. Training data from each of the plurality of sensors is recorded and sensor parameters are adjusted based on the training data. After the training episode, use data is sensed from the plurality of sensors during normal use of the seat by the user. The in-seat behavior of the user is characterized based on the use data which results in the generation of characterization data. At least one predetermined action is taken based on the characterization data.

6 Claims, 4 Drawing Sheets

(51) Int. Cl.
*A61B 5/00* (2006.01)
*A61B 5/103* (2006.01)

(56) References Cited

U.S. PATENT DOCUMENTS

| | | |
|---|---|---|
| 8,528,135 B2 | 9/2013 | Turo et al. |
| 9,149,211 B2 | 10/2015 | Mravyan et al. |
| 9,655,795 B2 | 5/2017 | O'Keefe et al. |
| 2014/0039351 A1 | 2/2014 | Mix et al. |
| 2014/0371635 A1* | 12/2014 | Shinar .................. A61B 5/6891 600/595 |
| 2015/0351981 A1 | 12/2015 | Szaonov |
| 2016/0183687 A1* | 6/2016 | Hoyt .................... A47C 31/126 297/217.2 |
| 2017/0161576 A1* | 6/2017 | Banno .................... B60K 28/06 |

\* cited by examiner

WHEELCHAIR IN-SEAT ACTIVITY TRACKER

CROSS-REFERENCE TO RELATED APPLICATION(S)

This application claims the benefit of U.S. Provisional Patent Application Ser. No. 62/372,331, filed Aug. 9, 2016, the entirety of which is hereby incorporated herein by reference.

STATEMENT REGARDING FEDERALLY SPONSORED RESEARCH

This invention was made with government support under agreement No. 90RE5000-01-00, awarded by the U.S. Department of Health and Human Services and under agreement No. W81XWH-13-1-0387, awarded by the Army Medical Research Center. The government has certain rights in the invention.

BACKGROUND OF THE INVENTION

1. Field of the Invention

The present invention relates to sensor units and, more specifically, to a sensor unit for sensing and characterizing forces placed on a chair by a user.

2. Description of the Related Art

Prolonged, static sitting leads to fatigue and discomfort, along with a host of health problems and increased mortality when it occurs over the long term. But prolonged static sitting is common to humans across leisure (e.g., airplane travel, television watching and video gaming) and occupational tasks (e.g., for truck drivers, office workers, fighter pilots, etc.) alike. Postural adjustments and movements provide relief to some of the consequences of prolonged sitting. Physiologically, movement offers improved circulation and is beneficial for joints and ligaments. Therefore, the ability to unobtrusively measure in-seat movements of varying magnitude and duration and to take action based on that information has the potential to improve comfort, fatigue, and job performance. One particular example of prolonged sitting is individuals who use wheelchairs as their primary means of mobility. In addition to discomfort, the combination of reduced mobility and impaired sensation results in a lifetime risk of developing pressure ulcers. In addition to the medical costs, the development of a pressure ulcer adversely impacts activities of daily living, employment and overall quality of life.

The formation and underlying causes of pressure ulcers are quite complex, with multiple influencing factors. However, tissue loading is the defining cause of pressure ulcers and distinguishes them from other insults such as vascular and ischemic ulcers. The mechanisms by which tissue loading leads to tissue breakdown have not been established, but current theories suggest that a combination of cell damage from prolonged deformation, ischemia of soft tissues, and a disruption in the equilibrium of the lymphatic system are involved. Longstanding research has clearly demonstrated that the damaging effects of pressure are related to both its magnitude and duration, which is consistent with the proposed mechanisms of damage. Generally, tissues can withstand higher loads for shorter periods of time.

Clinical interventions have been based upon the premise that both the magnitude and duration of loading are important. The impact of magnitude and duration of loading is influenced by an individual's intrinsic risk factors that impact tissues tolerance to loading. Intrinsic factors include the influences of nutrition, age, injury and disease, amongst others. Additionally, recent imaging studies have documented vast variations in buttocks anatomy, tissue type and quality, which will also influence the tissue response to loading. Because the magnitude and duration of loading are the defining causes of pressure ulcers, prevention strategies for wheelchair users routinely target these factors. Pressure magnitude is managed by the selection of wheelchair cushions, other support surfaces, and body posture as one rests upon these supporting surfaces. Duration of pressure is addressed via the frequency of turning and weight shifting activities as well as with the use of dynamic surfaces that actively redistribute pressure on the body surfaces.

To minimize the duration of pressure, wheelchair users who are at risk of developing sitting-acquired pressure ulcers are taught a variety of maneuvers to shift body weight off the buttocks using forward and side leans or lifting their buttocks off the cushion surface. A few studies have documented that these maneuvers are effective in reducing pressures and increasing blood flow to the buttocks tissues. Clinical guidelines recommend that persons perform pressure reliefs with varying durations and frequencies ranging from 15 to 30 seconds every 15 to 30 minutes to 60 seconds every hour.

A few studies have investigated self-reported measures of pressure relief behaviors but found no significant relationship with pressure ulcer occurrence. Self-reported behaviors might not have been accurate or sensitive enough to be adequately evaluated. Furthermore, protective weight shift behaviors may include other activities in addition to dedicated pressure reliefs, and were not considered during these studies. Indeed, many functional movements such as reaching and movement in the wheelchair seat during daily tasks have been shown to redistribute pressure off sites at-risk for pressure ulcer development while also increasing blood flow.

In order to further investigate the role of pressure reliefs in reducing pressure ulcer occurrence, it is important to understand the in-seat movements of wheelchair users. Research has been undertaken to understand how people change seated postures during occupational sitting, typically measuring movements over a short period of time. There is a need for having the ability to identify different types of in-seat movements, based on the magnitude, frequency, and duration of the movements. Typically, larger movements are typically done with a lower frequency than smaller movements. Most studies of the sitting behavior of wheelchair users have been limited to measurement of occupancy or complete offloadings.

Pressure measurement systems include devices that have been installed in wheelchairs that sense and report pressure from the user. However, such systems use sensors that are not placed in anthropometric locations and they are not trained by the users so as to be able to characterize the different types of in-seat movements of a specific user. Thus, they do not provide a precise characterization of the in-seat behavior of the user. Also, such systems are not retrofitable onto different wheelchairs and seats, including those with flexible upholstered or sling seats, as well as rigid seats.

Therefore, there is a need for an in-seat behavior that is retrofitable and that can be trained to characterize the movements of a specific user.

SUMMARY OF THE INVENTION

The disadvantages of the prior art are overcome by the present invention which, in one aspect, is a method of determining in-seat behavior of a user having a buttocks sitting on a seat, in which a sensor mat is placed on a location of the seat. The sensor mat includes a plurality of sensors that are distributed anthropometrically so as to be placed below predetermined anatomical sites of a typical user. At least one training episode in which the user assumes at least one predetermined posture for a predetermined amount of time is executed. Training data from each of the plurality of sensors is recorded and sensor parameters are adjusted based on the training data. After the training episode, use data is sensed from the plurality of sensors during normal use of the seat by the user. The in-seat behavior of the user is characterized based on the use data wherein characterization includes a spectrum of different types of activity (including selected ones of: longer duration activities, full unloading activities of a particular duration, partial unloading activities with a minimum duration and short transient movements), which results in the generation of characterization data. At least one predetermined action is taken based on the characterization data.

In another aspect, the invention is a system for sensing determining in-seat behavior of a user having a buttocks sitting on a seat that includes a platform and a cushion. A sensor mat is configured to be placed between the platform and the cushion. The sensor mat includes a plurality of sensors that are distributed anthropometrically so as to be placed below predetermined anatomical sites of a typical user. A data acquisition unit is configured to receive sensor data from the plurality of sensors. The data include training data collected from each of the plurality of sensors during at least one training episode in which the user has assumed at least one predetermined posture and use data collected during normal use by the user. A data analysis unit is responsive to the data acquisition unit and is configured to characterize the use data as a function of the training data. A device is configured to take a predetermined action when the data analysis unit has characterized the use data as conforming to predetermined criteria.

In yet another aspect, the invention is a chair for a user having a buttocks that includes a platform and a cushion, disposed above the platform, upon which the user sits. A sensor mat is disposed between the platform and the cushion. The sensor mat includes a plurality of sensors that are distributed anthropometrically so as to be placed below predetermined anatomical sites of a typical user. A data acquisition unit is configured to receive data from the plurality of sensors. The data include training data collected each of the plurality of sensors during at least one training episode in which the user assumed at least one predetermined posture and use data collected during normal use by the user. A data analysis unit is responsive to the data acquisition unit and is configured to characterize the use data as a function of the training data. A device is configured to take a predetermined action when the data analysis unit has characterized the use data as conforming to predetermined criteria.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Figure 1:
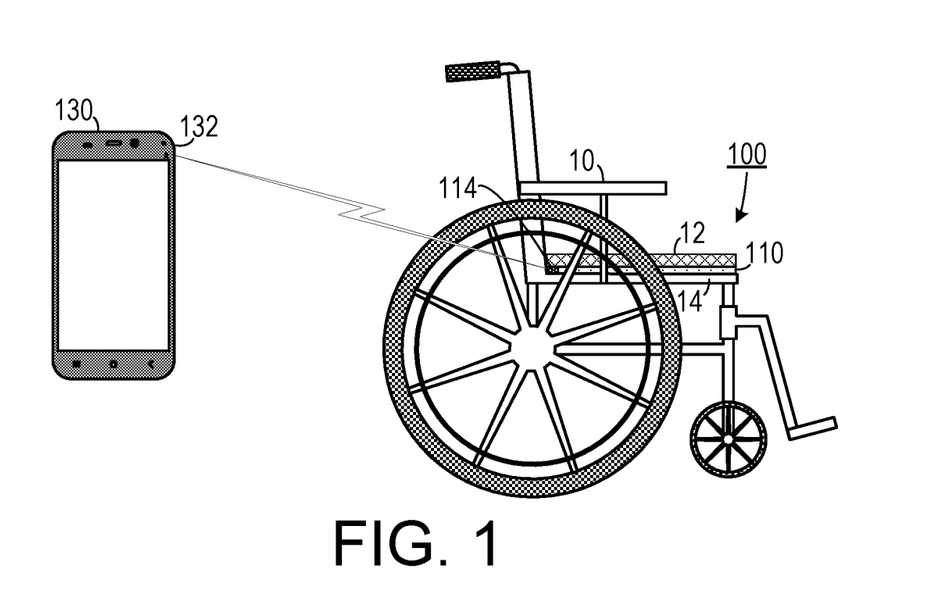
FIG. 1 is a schematic drawing showing one embodiment of an in-seat behavior sensor system.
Figure 2:
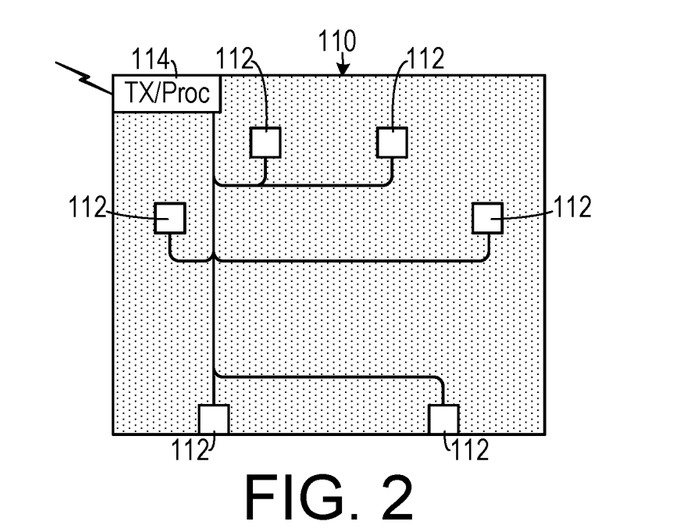
FIG. 2 is a schematic drawing showing one embodiment of a sensor mat.
Figure 3:
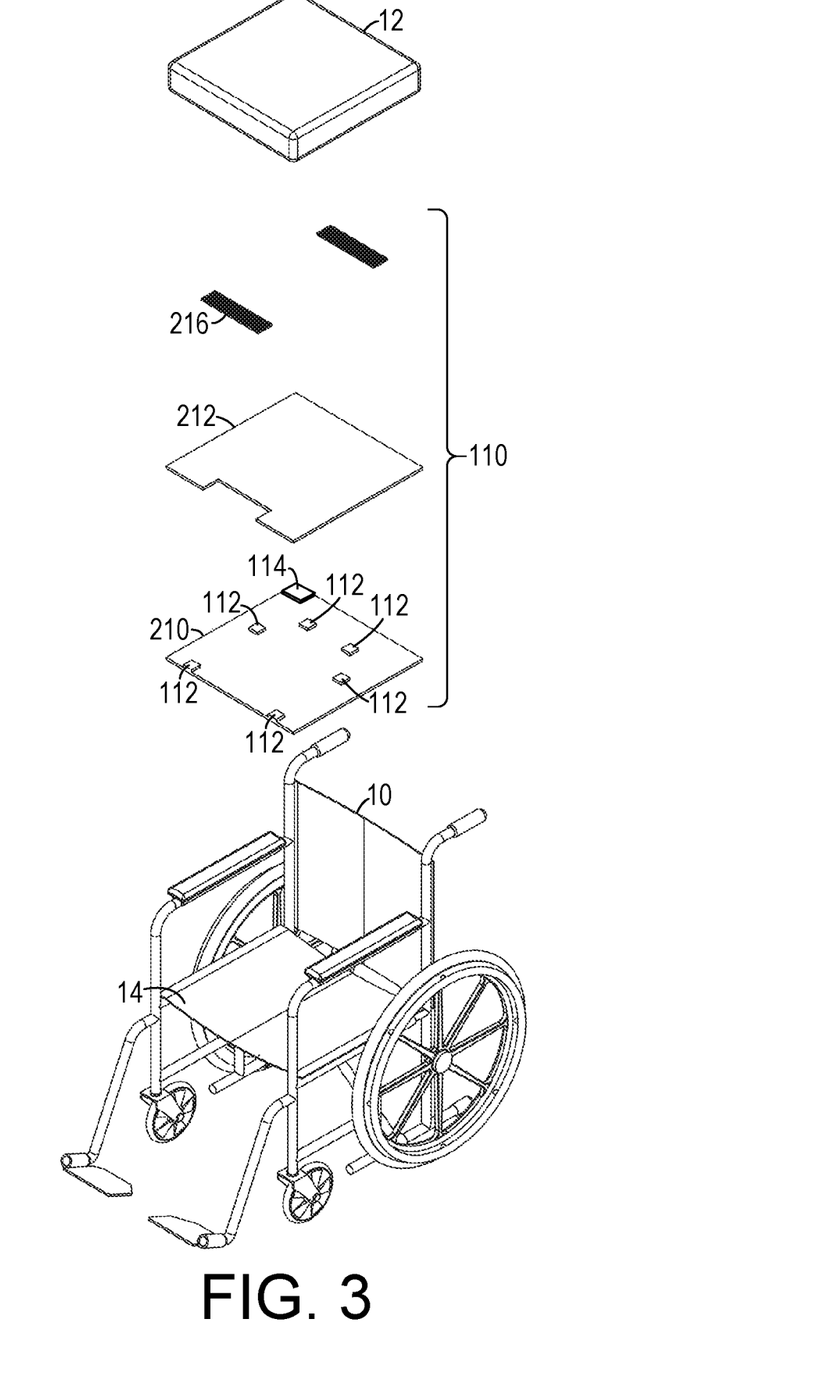
FIG. 3 is an exploded schematic drawing of the in-seat behavior sensor system shown in FIG. 1.

As shown in FIGS. 1-3, one embodiment of an in-seat behavior characterization system can include a seat, such as a wheelchair 10 that includes a platform 14 upon which a cushion 12 is placed. (In other embodiments, the seat could be, for example, an airline seat or one of many other types of seats.) A sensor mat 110 that includes a plurality of sensors is placed of the platform 14 underneath the cushion 12. The sensor mat 110 either includes a data acquisition and storing system that stores data from the sensors or a wireless system 114 for acquiring data from the sensors and transmitting it to a remote device 130, which includes a wireless receiving circuit 132, for storing and subsequently analyzing the sensor data. In the embodiment shown, the remote device 130 comprises a smart phone. However, in other embodiments, the remote device 130 could include a laptop computer, a tablet device, a desk top computer or a device connected to the receiving circuit via the global computer network.

The sensor mat 110 includes a plurality of sensors 112 (such as pressure sensors) that are distributed anthropometrically on a bottom layer 210 so as to correspond to specific anatomical parts of the user (e.g., the buttocks and the pelvis). A cover 212, such as a flexible waterproof cover is placed over the sensor mat 110 for protection. One or more hook-and-loop fastener strips 216 are affixed to the cover 212 to keep the sensor mat 110 in a steady relationship with the cushion 12. (As is readily understood by those of skill in the art, many other methods of coupling the sensor mat 110 to the cushion 12 can be employed without departing from the scope of the invention.) The bottom layer 210 and the cover 212 can be made of flexible materials so as to make the sensor mat 110 adaptable to both rigid seat platforms and flexible seat platforms. As a result, the sensor mat 110 is retrofitable to any type of wheelchair or other type of chair.

Figure 4:
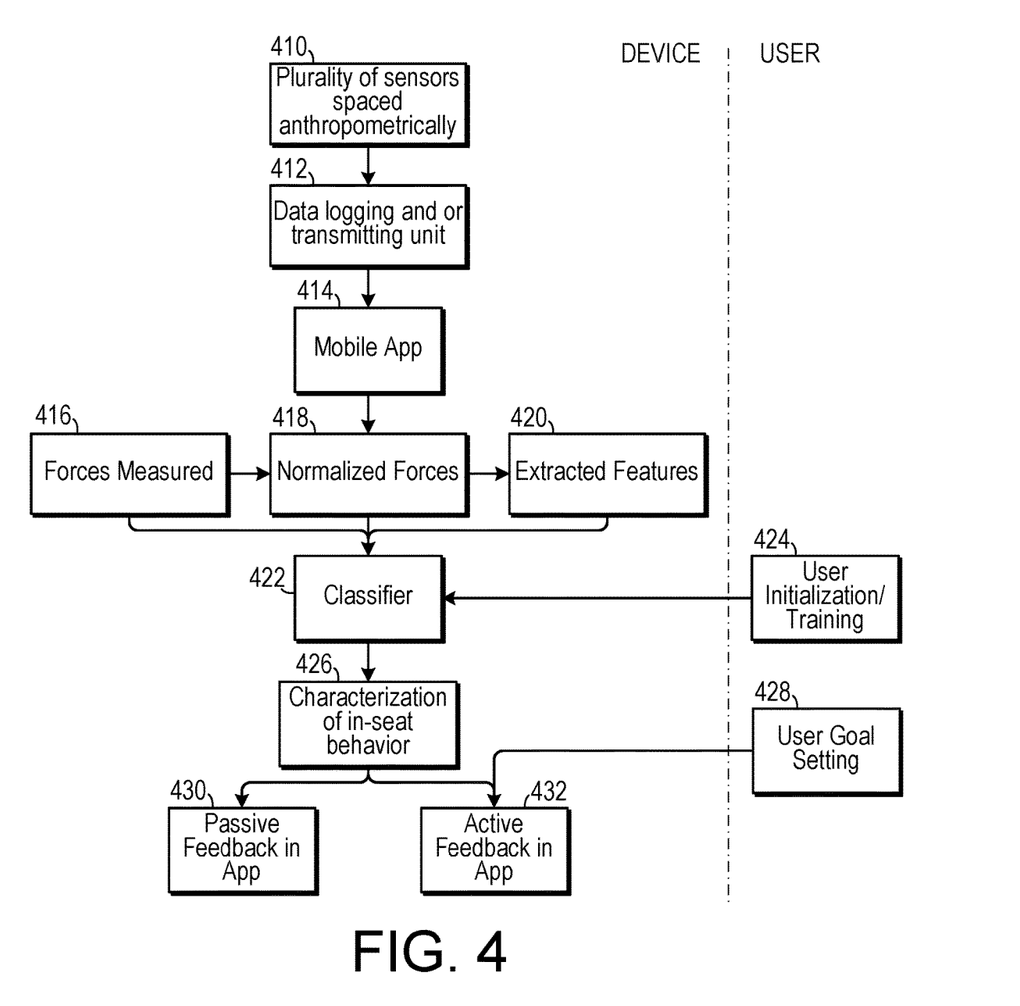
FIG. 4 is a block diagram showing certain features of an in-seat behavior sensor system.
Figure 5A:
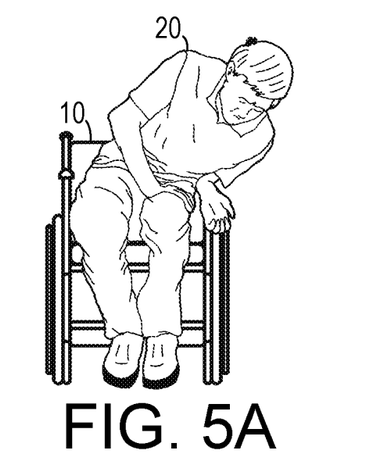
FIGS. 5A-5E are a series of schematic drawings showing different postures that can be assumed as part of a training event.
Figure 5B:
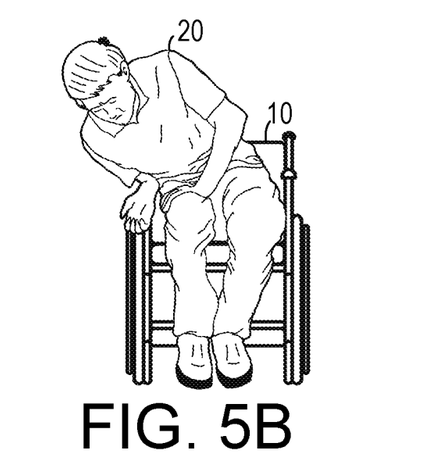
Figure 5C:
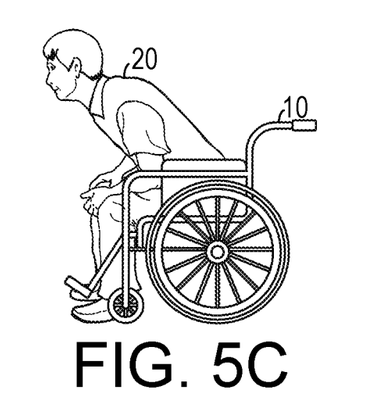
Figure 5D:
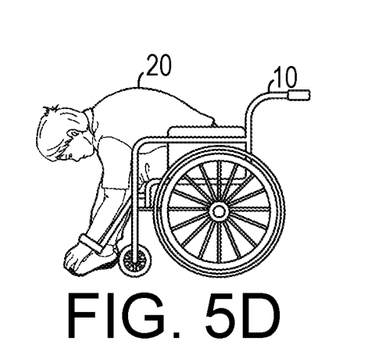
Figure 5E:
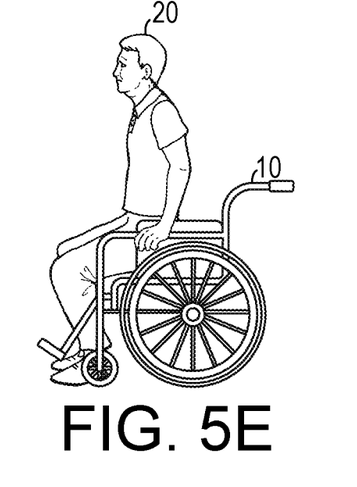

As shown in FIG. 4, the system uses sensors that are spaced anthropometrically 410 so as to correspond to the anatomical features of interest of an average human body. In some embodiments, the electronics are tethered to the mat whereas in other embodiments the electronics are included in the mat. A data logging and transmitting unit 412 transmits data from the sensors to a remote device, such as a smart phone running a mobile app 414. Forces are measured 416 and are processed using normalizing techniques 418 and features are extracted 420. Such features can include, for example, locations of centers of pressure experienced by the user.

The user goes through one or more initialization and training events 424, in which the user sits on the sensor mat in various different postures for predetermined amounts of time. The data from the sensor mat is acquired during the training events and parameters associated with the sensor mat data are adjusted so as to fine tune detection of the specific user's positions and movements.

Based in the parameter adjustment and data acquired during ordinary usage of the seat, the positions of the user are classified 422 and the user's behavior is characterized 426. For example, the system might characterize the user's behavior as maintaining a certain position for a predetermined amount of time.

In some embodiments, the system can provide passive feedback 430, such as providing overall behavior data to the user or to a clinician. Such data can be analyzed in preparing treatment plans for the user and for performing scientific studies involving in-seat behavior. In other embodiments, the user can set goals 428 (e.g., change from left-leaning position to right-leaning position every 15 minutes) and the system can provide active feedback 432 to the user to assist the user in achieving such goals. Such feedback can include verbal indications and alarms transmitted to the user or to a clinician via a mobile app when the use data indicate that a characterized weight shifting movement event has not occurred within the amount of time set as a goal.

Examples of some of the positions that can be used in training exercises and that can be detected by the system during normal usage are shown in FIGS. 5A-5E. Such positions can include, for example: lean to the left, lean to the right, lean forward slightly, lean fully forward, and support body with arms. In the training episode, the user will assume postures such as these for a predetermined amount of time and training data from each of the plurality of sensors is recorded. Based on this algorithm, parameters may be adjusted.

In one embodiment, the system can compensate for "sensor creep" in which the user's positional relationship to the sensors shifts due to movements by the user or by the equipment. The system can detect movement of the user with respect to the plurality of sensors over time and then adjust the use data to compensate for the movement of the user.

Advantages of the current system include the fact that the seat sensor mat can be placed underneath the wheelchair cushion to avoid any hindrance of cushion performance and to allow the use of commercial wheelchair cushions without modification. The seat sensors are placed based upon human anthropometry to accurately measure load and load distribution on the cushion by the wheelchair user during both static and dynamic seated postures. An algorithm capable of accommodating system creep over long durations of use can maintain the ability to accurately classify weight shift and in-seat movement activity. An algorithm is capable of classifying a continuum of weight-shifting activities ranging from partial load distribution resulting from leaning and reaching to complete unweighting of the cushion surface. The classification algorithm takes into account both magnitude and duration of loading to better distinguish different weight-shifting behaviors. Also, an algorithm can be used that is capable of monitoring the in-seat movement of a wheelchair users that results from transient re-distribution of cushion loading during dynamic changes in seated posture.

In one experimental embodiment, individuals with chronic spinal cord injury were recruited from rehabilitation facilities. Each subject's primary wheelchair was fitted with a custom-fabricated, eight-element Pressure Relief Monitoring (PRM) mat of force sensors. The 8 piezo-resistive force sensors (Vista Medical Ltd, Winnipeg, Calif.) were configured into two sets of 4 sensors and placed underneath the wheelchair cushion. Resistances measured by each sensor were converted to voltages using custom-fabricated circuitry and stored as voltage on a data logger (MSR Electronics GmbH). Signals were continuously sampled at 1 Hz with 8-bit resolution for the duration of the instrumented period, which was typically between 1 and 2 weeks. The data were retrieved at the end of this period.

A brief (approximately 10-15 minute) training protocol was used in this study to relate the loads and center of pressure movements measured under the wheelchair cushion with the pressures at the buttocks/cushion interface. The training protocol was conducted at the beginning of instrumentation, and repeated for some participants following the instrumentation period. Participants transferred out of their wheelchair, and the PRM mat was attached beneath their wheelchair cushion and an FSA interface pressure mat was placed on top of their wheelchair cushion. Participants performed a prescribed series of maneuvers to mimic weight shifts and functional in-seat movements. These maneuvers included leans with varying degrees of trunk movement to the front, left, and right. Subjects were also asked to adopt other postures and movements that they self-identified as commonly performed, and to move dynamically in their seats for one minute. Periods of stationary upright sitting and push-up pressure reliefs were interspersed among the leans. Interface pressure and PRM force data were simultaneously collected at 1 Hz during the training set and were later correlated to provide a ground truth for interpreting the PRM data as described below.

Following the completion of the training set, the interface pressure mat was removed and participants were instructed to proceed with their normal activities as if no instrumentation was present. Standard demographics questions were asked, as well as questions about mobility and seating equipment and how individuals utilized their equipment. Behavioral questions included the strategies participants used to increase seated comfort, the frequency and types of pressure reliefs performed, and the purposes for which they transferred.

The PRM mat data, consisting of eight independent time series of force, were initially reduced to a four-feature time series dataset that were used in further processing. These features included the maximum forces measured on the left and right sides, and the location of the center of pressure (CoP) on the mat in the medial-lateral and anterior-posterior directions. The total PRM load was calculated as the sum of all 8 sensor measurements, and was used to determine wheelchair occupancy and complete offloading.

One challenge in processing long-term seated force data can be that the measurements during inactive sitting can change over time due to several factors, including differences in where the person sits on the cushion, drift in the sensor responses, and creep in the system. Given the rationale that weight shifts consist of transient changes in sitting posture, analysis necessitated a continually defined baseline loading condition that reflected an upright posture. Baseline series were computed for each feature by applying a zerodelay low-pass filter to the measured force time series from which the features were computed over the periods of occupancy. A corner frequency of 0.005 Hz (1/200 s) was selected for the baseline filter from an inspection of multiple data sets. In-seat movement and weight-shift features were then based upon deviations from this baseline series.

A similar approach was used to process the interface pressure training data. First, the interface pressure data was used to calculate the peak pressure index (PPI), or the peak pressure in a 9-10 $cm^2$ region underneath each ischial tuberosity, and the center of pressure (indicative of the center of mass) in the medial-lateral and anterior-posterior directions. In the case of the training data, the baseline was computed using the measurements during known upright sitting segments. Normalized interface pressure values were used as ground truth for the training protocol. Each set of PRM features was classified as a weight shift if the normalized interface pressure was reduced by more than 30% from upright sitting.

A spectrum of measures that vary in magnitude and duration of unloading was chosen. The magnitude of unloading was determined by associating the PRM features with ground truth status using interface pressures from the training set measurements. These measures included: wheelchair occupancy, transfers out of the chair, pressure relief frequency, weight shift frequency, and in-seat activity frequency.

Wheelchair occupancy was defined when more than 10% of the total upright PRM force data was measured, a threshold that was validated using the interface pressure data collected during the training set. Full off-loading was defined by ≥90% reduction in total PRM force. This full off-loading state was further categorized using its duration: Offloading for more than 2 minutes was considered a transfer out of the wheelchair while offloading lasting between 15 and 120 seconds was defined as a Pressure Relief (PR). Weight shifts (WS) were defined as a 30%-90% reduction in the interface pressure PPI values compared to upright sitting. In the training set data, all PRM features were classified as a WS or upright sitting according to the associated normalized interface pressure PPI values. PRM features from the daily data were then classified by comparing the PRM features to the training set's PRM features and associated ground-truth status of upright sitting or WS. A WS was confirmed when this pressure reduction occurred on at least one ischial tuberosity and lasted at least 15 seconds.

In-plane motion of the CoP measured on the PRM mat was used as a proxy for subject in-seat movement. The in-plane distance traversed by the CoP was calculated as the square root of the sum of the squares of the finite differences of the absolute medial-lateral and anterior-posterior CoP locations over a 5-sec window. To equilibrate this distance across subjects and cushions, the relationship between the total CoP distances traveled as measured on the interface pressure mat and on the PRM mat during training was calculated. The in-plane motion of the CoP measured on the PRM mat throughout the data collection period was multiplied by the ratio described previously. When the distance traveled over 5 seconds was greater than 5.4 cm, the time point was considered "active" (i.e., In-Seat Activity). This distance equates to the length of 2 sensors on the interface pressure mat used during this part of data collection. It was determined empirically with the objective to define a threshold to define active in-seat movement.

The frequency of WSs, PRs and In-Seat Activity were calculated for each day as the number of respective events divided by the number of hours spent in the wheelchair. Finally, an Upright Sitting time was defined for each day. This was the longest duration the individual was seated in their wheelchair without performing a PR or a WS. Wheelchair occupancy and in-seat movement metrics were summarized over all subject days. Coefficient of variation was also computed across subject days (across-subject variation), as well as individually for each subject (within-subject variation). The individual subject coefficients of variation were then averaged to report overall within-subject variation.

In this experimental study, data was collected on 37 participants. Of these, 9 participants were excluded from the present analysis due to missing data, sensor malfunctions, or failure to collect a training set. From these 28 participants, we collected a total of 208 complete days of data with 16 of these days exhibiting fewer than 4 hours spent in the wheelchair. Because those days were inconsistent with full-time use, the remaining 192 days were analyzed.

The 28 participants were full time wheelchair users, predominantly with a diagnosis of SCI (n=25). Injuries were mostly thoracic, with only two participants having cervical injuries. Level of function among participants was similar though, as all participants used a wheelchair full-time, and were independent in wheelchair use and transfer (only 1 participant required a lift or hoist for his transfers). Eleven of the participants had a history of multiple pelvic pressure ulcers.

All participants in this study used ultra-light manual wheelchairs. They sat on a variety of wheelchair cushions, with Roho products being the most common (n=11), along with Jay (n=5), Varilite (n=4), Ride (n=3), Matrx (n=2), and other products (n=2). Wheelchair cushions varied in age, with an average (SD) of 2.3 (2.0) years, and ranging from 1 week to 7 years old.

When asked what strategies were used to increase seated comfort, participants reported transferring to other surfaces and/or readjusting their posture within the wheelchair seat. In response to questions about weight shift and transfer behaviors, 86% of participants reported doing complete (depression or push-up) lifts for pressure relief, while approximately 35-45% reported performing front leans, partial leans, and side leans. The majority of participants in this study transferred out of their wheelchair to perform bowel/bladder routines (n=25), to shower (n=27), to travel in a vehicle (n=26), to sit in a different chair (i.e. a couch or recliner) (n=21). Only 6 participants reported transferring to sit in a different wheelchair.

Over 192 days in which participants spent at least 4 hours in their wheelchairs, participants spent an average of 10.5 hours per day in their wheelchairs, which is consistent with the inclusion criteria of full-time wheelchair use. PR Frequency ranged from 0 to 2.8 times per hour, while WS frequency ranged from 0 to 15.4 times per hour, though both frequencies were skewed towards 0 with median frequencies of 0.2 and 1.8, respectively. In order to compare the WS and PR frequencies to the clinical guidelines, which recommend pressure reliefs every 15 to 60 minutes, the 95% confidence intervals of the average time between WSs and PRs are presented. The intervals suggest that PRs were not done at a frequency meeting clinical guidelines, with a 95% confidence interval of [214, 296] minutes between PRs on days when at least 1 PR was done. On the other hand, WSs did meet the recommendation of performing one every 60 minutes with a 95% confidence interval of [49, 75] minutes between WSs.

In addition to the typical or average frequency of WSs, it is important to consider the range and distribution of behaviors within a day. For example, even though WS frequency exceeded two per hour, it does not guarantee two WSs every hour. Therefore, the longest period of time a participant spent seated between unloading events (Upright Sitting) was calculated for each day. On the average day, subjects had an Upright Sitting segment lasting 140 minutes (SD=84 minutes) without performing a weight shift or pressure relief.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method of determining in-seat behavior of a user having a buttocks sitting on a seat, comprising the steps of:
   (a) placing a sensor mat on a location of the seat, wherein the sensor mat includes a plurality of sensors that are distributed anthropometrically so as to be placed below typical anatomical sites that impart load onto the seat surface during different seated postures;
   (b) prior to normal use of the sensor mat, executing at least one training episode in which the user is instructed to adopt different postures including sitting upright and performing varying degrees of trunk movement in forward, left and right directions that alter force distribution at a buttocks-seat interface, while recording force values from the sensor mat in order to establish a relationship between postural shifts and force redistribution as measured by the plurality of sensors recording training data from each of the plurality of sensors and using the training data from the sensors to classify in-seat behaviors of the user;
   (c) after the training episode, sensing use data from the plurality of sensors during normal use of the seat by the user;
   (d) characterizing the in-seat behavior of the user based on the use data wherein characterization includes a spectrum of different types of activity resulting from both volitional and non-volitional weight shifts (including selected ones of: longer duration activities, full unloading activities of a particular duration, partial unloading activities with a minimum duration and short transient movements), thereby generating characterization data; and
   (e) taking at least one predetermined action based on the characterization data.

2. The method of claim 1, wherein the step of taking at least one predetermined action comprises instructing the user to perform a weight shifting behavior when the use data indicate that a characterized movement event has not occurred.

3. The method of claim 1, further comprising the step of recording and analyzing the use data.

4. The method of claim 1, further comprising the steps of:
   (a) detecting movement of the user with respect to the plurality of sensors over time; and
   (b) adjusting the use data to compensate for changes in sensor output when no postural shift occurs.

5. The method of claim 1, wherein the seat comprises a chair having platform upon which rests a cushion and wherein the step of placing a sensor mat on a location of the seat that has fixed physical parameters comprises the step of placing the sensor mat between the platform and the cushion.

6. The method of claim 1, wherein the seat comprises a wheelchair.

* * * * *

UNITED STATES PATENT AND TRADEMARK OFFICE
CERTIFICATE OF CORRECTION

PATENT NO. : 10,357,186 B2
APPLICATION NO. : 15/672688
DATED : July 23, 2019
INVENTOR(S) : Sharon Eve Sonenblum, James S. Martin and Stephen Sprigle Page 1 of 1

It is certified that error appears in the above-identified patent and that said Letters Patent is hereby corrected as shown below:

In the Specification

Column 1, Lines 15-20, please replace:
"This invention was made with government support under agreement No. 90RE5000-01-00, awarded by the National Institutes of Health and under agreement No. W81XWH-13-1-0387, awarded by the Army Medical Research Center. The government has certain rights in the invention."

With:
--This invention was made with government support under agreement No. W81XWH-13-1-0387, awarded by the Army Medical Research Center. The government has certain rights in the invention.--

Signed and Sealed this
Thirteenth Day of October, 2020

Andrei Iancu
*Director of the United States Patent and Trademark Office*